US007221730B2

(12) United States Patent
Goto et al.

(10) Patent No.: US 7,221,730 B2
(45) Date of Patent: May 22, 2007

(54) MULTI-ROW DETECTOR X-RAY CT APPARATUS AND METHOD FOR CREATING TOMOGRAM

(75) Inventors: Taiga Goto, Kashiwa (JP); Osamu Miyazaki, Moriya-machi (JP)

(73) Assignee: Hitachi Medical Corporation, Tokyo (JP)

( * ) Notice: Subject to any disclaimer, the term of this patent is extended or adjusted under 35 U.S.C. 154(b) by 0 days.

(21) Appl. No.: 10/493,678

(22) PCT Filed: Oct. 23, 2002

(86) PCT No.: PCT/JP02/10997

§ 371 (c)(1),
(2), (4) Date: Apr. 23, 2004

(87) PCT Pub. No.: WO03/034920

PCT Pub. Date: May 1, 2003

(65) Prior Publication Data

US 2004/0258197 A1    Dec. 23, 2004

(30) Foreign Application Priority Data

Oct. 24, 2001  (JP) ............................. 2001-326669

(51) Int. Cl.
*A61B 6/00* (2006.01)
(52) U.S. Cl. .............................. 378/15; 378/4; 378/901
(58) Field of Classification Search .............. 378/4–20, 378/901
See application file for complete search history.

(56) References Cited

U.S. PATENT DOCUMENTS

| | | | |
|---|---|---|---|
| 5,513,236 A | 4/1996 | Hui | 378/15 |
| 5,541,971 A | 7/1996 | Saito | 378/15 |
| 5,559,847 A | 9/1996 | Hu et al. | 378/4 |
| 5,825,842 A * | 10/1998 | Taguchi | 378/15 |
| 5,838,756 A * | 11/1998 | Taguchi et al. | 378/4 |
| 5,974,110 A | 10/1999 | Hu | 378/19 |
| 6,236,707 B1 | 5/2001 | Flohr et al. | 378/15 |
| 6,252,926 B1 | 6/2001 | Flohr et al. | 378/15 |
| 6,400,790 B1 * | 6/2002 | Ohnesorge et al. | 378/15 |
| 6,819,736 B1 * | 11/2004 | Bruder et al. | 378/15 |
| 2005/0094760 A1 * | 5/2005 | Hagiwara | 378/4 |

FOREIGN PATENT DOCUMENTS

| | | |
|---|---|---|
| DE | 19547277 | 7/1996 |
| DE | 19647435 | 6/1997 |
| DE | 19854445 | 5/1999 |

(Continued)

*Primary Examiner*—Edward J. Glick
*Assistant Examiner*—Jurie Yun
(74) *Attorney, Agent, or Firm*—Cooper & Dunham LLP

(57) ABSTRACT

An X-ray CT apparatus comprising a scanner that includes an X-ray source and an X-ray detector having two-dimensionally arranged X-ray detector elements, disposed on the opposite side of the subject to the X-ray source and carries out helical scanning around the revolving axis and an image processor for creating a tomogram of the subject from the data collected by helical scanning using the X-ray detector, wherein the image processor creates a tomogram by reconstructing an image from data on the subject including a plurality of sets of projection data of different phases of helical scanning at the same point on the revolving axis and adding the reconstructed images of different phases, whereby a good image is created while suppressing aritifacts.

13 Claims, 13 Drawing Sheets

FOREIGN PATENT DOCUMENTS

| | | |
|---|---|---|
| DE | 19832275 | 1/2000 |
| DE | 19832276 | 1/2000 |
| JP | 0819532 | 1/1996 |
| JP | 08263638 | 10/1996 |
| JP | 09224930 | 9/1997 |
| JP | 11276473 | 10/1999 |
| JP | 200023966 | 1/2000 |
| JP | 200037379 | 2/2000 |
| JP | 200051205 | 2/2000 |
| JP | 200278702 | 3/2000 |
| JP | 2000225114 | 8/2000 |
| JP | 2001346794 | 12/2001 |
| WO | WO0128425 | 4/2001 |

\* cited by examiner

HELICAL SCANNING

FOCAL TRACK

NORMAL SCANNING

FOCAL TRACK

180-DEGREE RECONSTRUCTION USING FAN BEAM

180-DEGREE RECONSTRUCTION USING PARALLEL BEAM

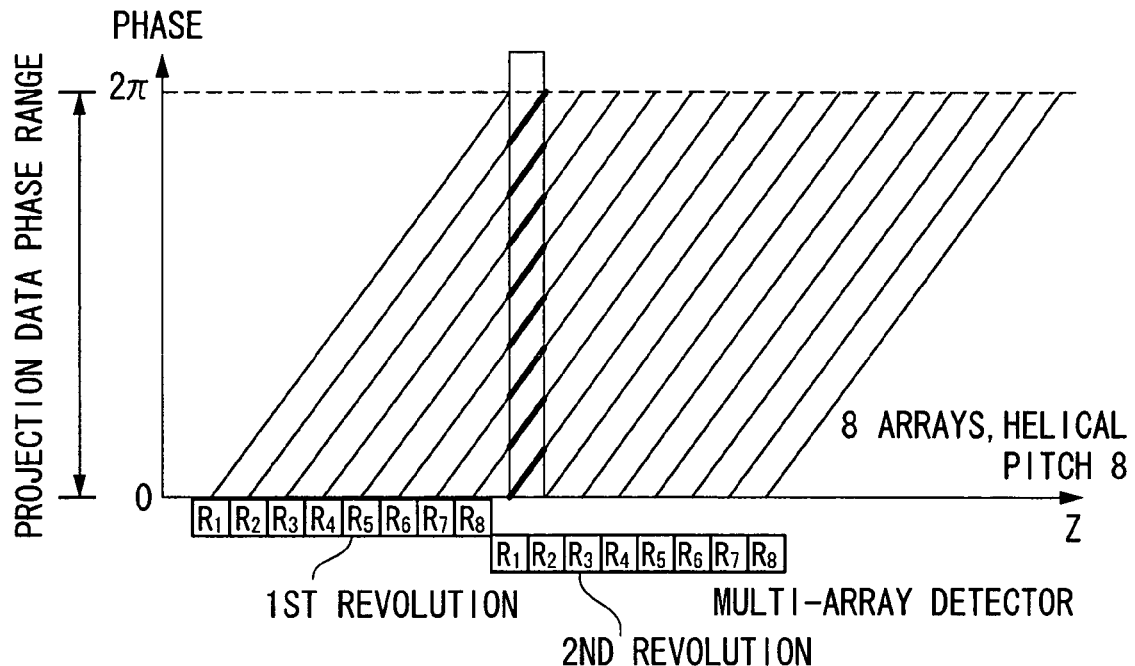
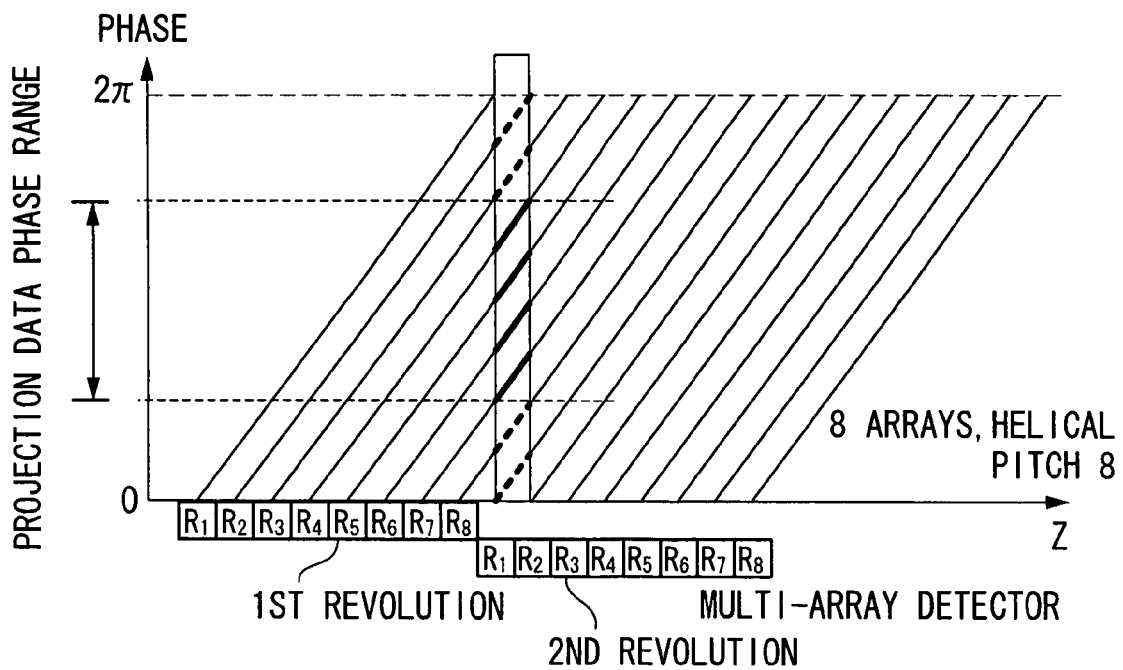

$0\pi$ PHASE IMAGE $\pi/6$ PHASE IMAGE $\pi/3$ PHASE IMAGE $\pi/2$ PHASE IMAGE

PHANTOM CROSSSECTION

HELICAL MEASURING DIAGRAM (180-DEGREE RECONSTRUCTION)

WEIGHTING FUNCTION (180-DEGREE RECONSTRUCTION)

HELICAL MEASURING DIAGRAM (PHASE ADDITION METHOD)

WEIGHTING FUNCTION (PHASE ADDITION METHOD)

π/2 PHASE IMAGE

3π/4 PHASE IMAGE

π PHASE IMAGE

DIFFERENT PHASE DATA ADDITION IMAGE

METHOD OF CREATING PHASE PROJECTION DATA

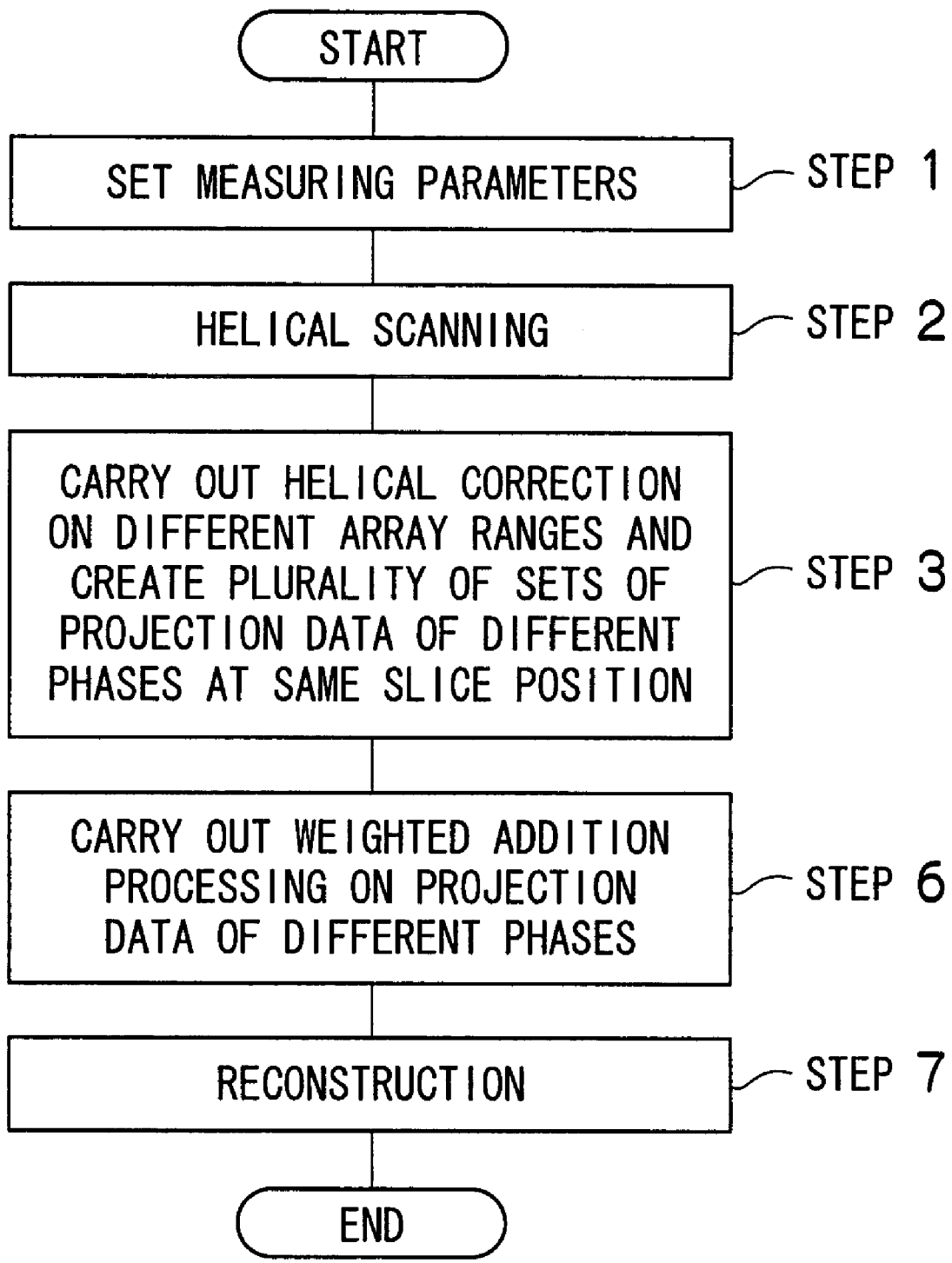

MULTI-ROW DETECTOR X-RAY CT APPARATUS AND METHOD FOR CREATING TOMOGRAM

TECHNICAL FIELD

The present invention relates to computerized tomography (CT) which obtains a tomogram by detecting transmitted X-rays from a subject irradiated with X-rays and subjecting the measured data obtained to image processing using a computer, and more particularly, to a multi-array detector X-ray CT apparatus having a multi-array detector made up of a plurality of arrays of detector elements and a method for creating the tomogram.

BACKGROUND ART

The mainstream of a current X-ray CT apparatus is an R/R-type (third-generation) CT apparatus which includes an X-ray source and an arc-shaped detector oriented toward the focal point of this X-ray source disposed on the opposite side of a subject to be examined to the X-ray source. X-rays from the X-ray source are collimated, formed into a fan-shaped X-ray beam and irradiated onto the image-taking cross section of the subject. An image-taking operation is carried out by revolving and measuring transmitted X-rays attenuated by the subject. A measuring operation is carried out at angle intervals of approximately 0.1 to 0.5 degrees of the revolution to obtain projection data of, for example, a total of 600 to 1200 channels.

The detector is made up of many detector elements and outputs of the respective elements are collected as digital data by a measuring circuit to constitute data (view) corresponding in number to the elements for each measuring angle. This view data is transferred successively from a revolving system to a stationary system through a transmission path. The transferred measured data is subjected to preprocessing such as characteristic correction of detection elements, beam correction or log conversion, etc., by an image processor in the stationary system and then reconstructed as a tomogram according to a publicly known algorithm such as a filter correction back projection method.

As one application example of such an X-ray CT apparatus, helical CT is known which enables high-speed inspection by carrying out measurements while moving a table on which a subject is laid simultaneously with revolutions of an X-ray source and detector. In such helical CT which helically scans the subject, acquiring a tomogram of a specific cross section requires the data of the cross section to be obtained from the helically obtained data through interpolation and such an interpolation processing technique is disclosed in, for example, in U.S. Pat. No. 4,789,929. Applying interpolation processing makes it possible to reduce artifacts due to movements.

Furthermore, multi-slice CT is available which divides the detector into a plurality of arrays and enables projection data of a plurality of cross sections to be measured simultaneously. The multi-slice CT simultaneously collects as many views as arrays, and can thereby take tomographic images of a plurality of cross sections in the case of normal table fixed scanning.

When a helical scanning is carried out using this multi-slice CT, it is necessary to carry out interpolation processing as with a single slice or reconstruct slices with weights equivalent thereto assigned.

U.S. Pat. No. 5,541,970 discloses a case of constructing weighting factors to achieve interpolation with the closest opposite beam and realizing helical correction. On the other hand, Japanese Patent Application Publication No. 9-285460 proposes a method for enhancing continuity by smoothing weighting factors in the Z-axis direction. However, these conventional multi-slice CT apparatuses do not have expandability in their helical scanning such that changes in the relationship between the number of detector arrays and helical pitch are not handled, and interpolation dimensions are not increased.

Therefore, the inventors of this patent application have disclosed a multi-slice X-ray CT apparatus to solve the above described problems in International Publication WO01/28425. While moving a subject in the direction of the body axis and rotating an X-ray source and detector arrays, this CT apparatus carries out a helical scanning for measuring X-rays which have passed through the subject, estimates a virtual detector array to complement the number of detector arrays when the helical pitch (ratio of the distance the subject moves when the X-ray source and the detector array make one rotation to the distance between the detector arrays) is greater than the number of detector arrays, distributes weights set for this virtual detector array to the weights of projection data of a real detector used to obtain the projection data of the virtual detector array. This CT apparatus is supposed to reconstruct a tomogram using projection data obtained from all the detectors of the plurality of detector arrays. Consequently, the number of the detector arrays is fixed and the relationship between the helical pitch and the number of the detector arrays is not optimized, and therefore many artifacts occur and the image quality characteristic changes irregularly when the helical pitch is changed (that is, the image quality characteristic does not change linearly with respect to the helical pitch). Especially when the number of detector arrays used for measurements and the helical pitch are the same, the image quality deteriorates a great deal. Furthermore, strong artifacts may be generated due to discontinuity of projection data at a specific phase (specific rotation angle of the X-ray source focus). Thus, in the X-ray CT apparatus disclosed in above described WO01/28425, the image quality characteristic changes not linearly but irregularly with respect to the helical pitch despite the fact that a weighting function is used according to the same rules for the number of detector arrays and helical pitch. This is attributable to the fact that the number of detector arrays used is constant all the time. If the image quality characteristic changes irregularly with respect to the helical pitch, it is not possible to adjust the helical pitch according to the desired image quality (intensity of artifacts). That is, it is more difficult to optimize the helical pitch for acquiring the desired image quality.

The present invention has been implemented in view of such circumstances and it is an object of the present invention to provide a multi-array detector X-ray CT apparatus and a method for creating a tomogram capable of suppressing artifacts and acquiring a good image.

DISCLOSURE OF THE INVENTION

In order to attain the above described subject, the X-ray CT apparatus according to the present invention comprises a scanner that includes an X-ray source and an X-ray detector having two-dimensionally arranged X-ray detector elements, disposed on the opposite side of the X-ray source interposing a subject to be examined therebetween and provided for measuring X-rays passed through the subject irradiated from the X-ray source onto the subject and carries out helical scanning by rotating the X-ray source and the X-ray detector relative to the subject around the revolving axis and moving the subject relative to the X-ray source and the X-ray detector along the revolving axis, and an image processor for creating a tomogram of the subject from projection data collected by helical scanning using the X-ray detector, wherein an image processor creates a tomogram by reconstructing an image from data on the subject including a plurality of sets of projection data of different phases of helical scanning at the same point on the revolving axis.

Furthermore, the X-ray CT apparatus according to the present invention comprises a scanner that includes an X-ray source and an X-ray detector having two-dimensionally arranged X-ray detector elements, disposed on the opposite side of the X-ray source interposing a subject to be examined therebetween and provided for measuring X-rays passed through the subject irradiated from the X-ray source onto the subject and carries out helical scanning by rotating the X-ray source and the X-ray detector relative to the subject around the revolving axis and moving the subject relative to the X-ray source and the X-ray detector along the revolving axis, and an image processor for creating a tomogram of the subject from the projection data collected by helical scanning using the X-ray detector, wherein the image processor creates a tomogram by reconstructing images of different phases from projection data of helical scanning at an identical point on the subject on the revolving axis and adding the reconstructed images of different phases.

The image processor preferably reconstructs an image from data obtained by assigning weights to the plurality of sets of projection data of different phases using weighting functions which are functions of the phase of helical scanning and combining the sets of projection data.

The data combined with weights assigned using the weighting function is preferably created from data of different phases from 0 to substantially $\pi/2$.

The image processor preferably includes a selection device that selects a plurality of sets of projection data of different phases from the plurality of the two-dimensionally arranged X-ray detector element arrays and reconstructs an image using the detected data of the element arrays selected by the selection device and data opposite to the detected data.

The plurality of the reconstructed images of different phases are preferably 180-degree reconstructed images.

The method for creating a tomogram according to the present invention is a method for creating a tomogram of a subject by revolving an X-ray source relative to a subject around a revolving axis and carrying out helical scanning which moves the X-ray source relative to the subject along the revolving axis from the projection data collected by an X-ray detector made up of a plurality of two-dimensionally arranged detector elements for measuring X-rays which have been irradiated from the X-ray source onto the subject and have passed through the subject, comprising a step of setting measuring parameters of the projection data, a step of obtaining projection data by carrying out helical scanning based on the measuring parameters, a step of creating projection data of a plurality of different phases of helical scanning at an identical point on the subject on the revolving axis from the projection data, a step of creating a plurality of reconstructed images at the same point on the revolving axis of the subject using the projection data of a plurality of phases created and a step of creating a reconstructed/added image by assigning weights and adding the plurality of reconstructed images created.

The step of creating the projection data of a plurality of different phases preferably comprises a step of setting the identical point of the reconstructed subject on the revolving axis, a step of deciding the range of the plurality of two-dimensionally arranged X-ray detector element arrays of the data used for reconstruction of the set identical point, a step of deciding a phase range corresponding to the range of the decided X-ray detector element arrays, a step of acquiring the data of the array range and phase range as phase data and a step of acquiring helically corrected projection data by creating and applying a weighting function to the phase data.

The weighting function is preferably a function of the phase of helical scanning.

The phase range of the weighting function is preferably $\pi$ or more.

The method for creating a tomogram according to the present invention is a method for creating a tomogram of a subject by revolving an X-ray source relative to the subject around a revolving axis and carrying out helical scanning which moves the X-ray source relative to the subject along the revolving axis from the projection data collected by an X-ray detector made up of a plurality of two-dimensionally arranged detector elements for measuring X-rays which have been irradiated from the X-ray source onto the subject and have passed through the subject, comprising a step of setting measuring parameters of the projection data, a step of obtaining projection data by carrying out helical scanning based on the measuring parameters, a step of creating projection data of a plurality of different phases of helical scanning at an identical point on the subject on the revolving axis from the projection data, a step of carrying out weighted addition processing on the projection data of a plurality of phases created and a step of creating a reconstructed image using the projection data obtained through the weighted addition processing.

According to the present invention, by combining data of different phases or images reconstructed from the data, it is possible to suppress artifacts and obtain a good image.

BRIEF DESCRIPTION OF THE DRAWINGS

FIG. 6(*a*) and FIG. 6(*b*) respectively illustrate projection data phase ranges of 360-degree reconstruction and 180-degree reconstruction by the multi-array detector CT apparatus;

FIG. 13 is a flow chart illustrating a method for creating phase projection data.

BEST MODE FOR CARRYING OUT THE INVENTION

With reference to the attached drawings, embodiments of the present invention will be explained in detail below.

Figure 1:
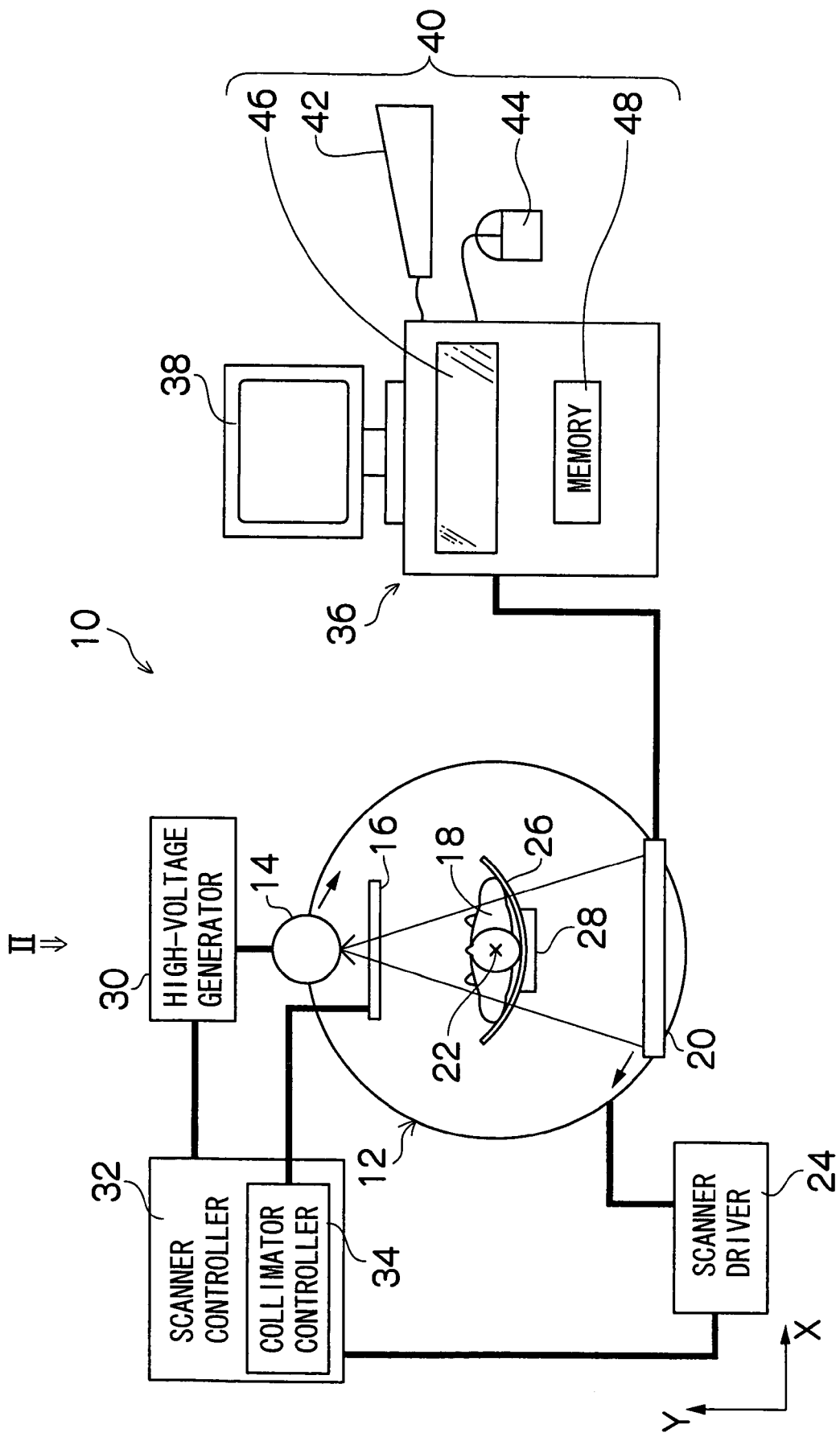
FIG. 1 shows an overall construction of a multi-array detector X-ray CT apparatus according to an embodiment of the present invention.

FIG. 1 is a schematic block diagram of a multi-array detector X-ray CT apparatus 10 to which an embodiment of the present invention is applied. The X-ray CT apparatus 10 is provided with a scanner 12 including an X-ray generator 14 for generating X-rays, a collimator 16 for collimating X-rays generated by the X-ray generator 14 and irradiates a subject 18 with the collimated X-rays and an X-ray detector 20 for detecting X-rays passed through the subject 18. The scanner 12 can be rotated around an axis 22 by a scanner driver 24. The subject 18 is laid on a subject table 26 such that the body axis of the subject 18 substantially matches the axis 22. The subject table 26 can be moved along the axis 22 by a subject table moving mechanism 28.

The X-ray generator 14 is supplied with a high voltage for generating X-rays from a high-voltage generator 30. The scanner driver 24, subject table moving mechanism 28 and high-voltage generator 30 are controlled by a scanner controller 32 and the collimator 16 is controlled by a collimator controller 34 included in the scanner controller 32.

Figure 2:
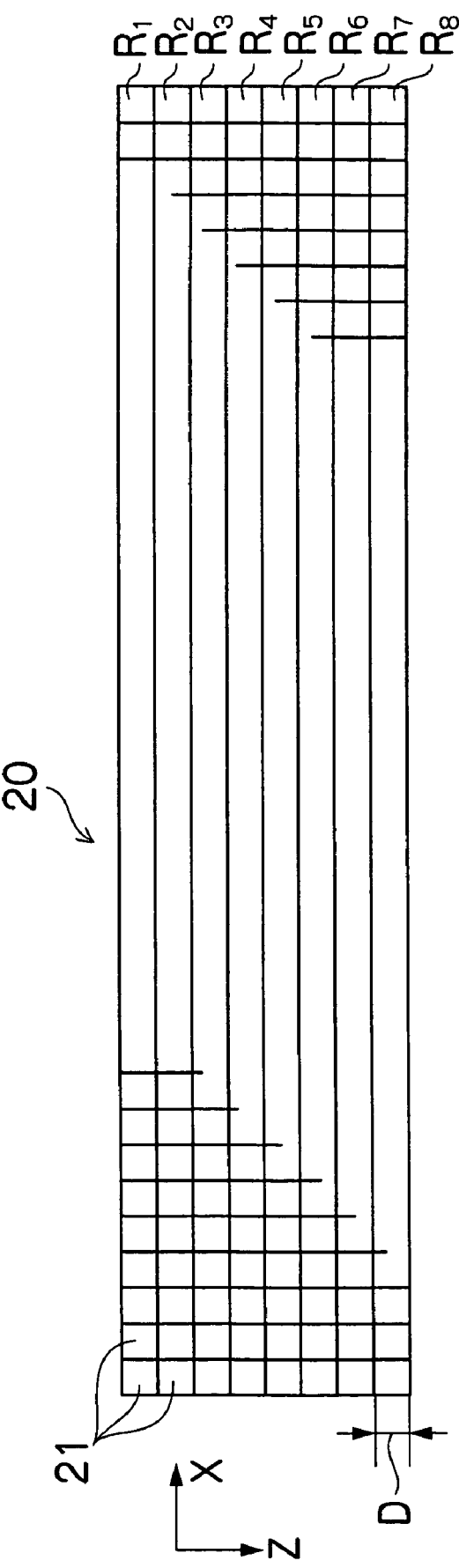
FIG. 2 is a conceptual diagram of an X-ray detector.

FIG. 2 is a conceptual diagram of the X-ray detector 20 viewed from the direction II at the top of FIG. 1. The X-ray detector 20 includes a plurality of detector element arrays R1 to R8, eight detectors in this embodiment, lined in the Z-direction, along the axis 22, in parallel to the X-direction. The width D of each of the detector element arrays R1 to R8 in the Z-direction is called a "detector collimation thickness." Each of the detector element arrays R1 to R8 is constructed of a plurality of detector elements 21. Each of the detector elements 21 generates an electric signal indicating the intensity of an incident X-ray beam and outputs the signal to an image processor 36 (see FIG. 1). These electric signals are data indicating the degree of attenuation of X-ray beams which have passed through the subject 18, hereinafter referred to as "projection data", and the image processor 36 reconstructs a tomogram of the subject 18 from the projection data and displays it on a display device 48. The image processor 36 is provided with an input apparatus 40 used to set measuring parameters, etc. This input apparatus 40 includes a keyboard 42, a mouse 44 and a touch panel 46, etc. Furthermore, a memory 48 which stores measuring parameters, etc., may partly form the input apparatus 40.

Figure 3:
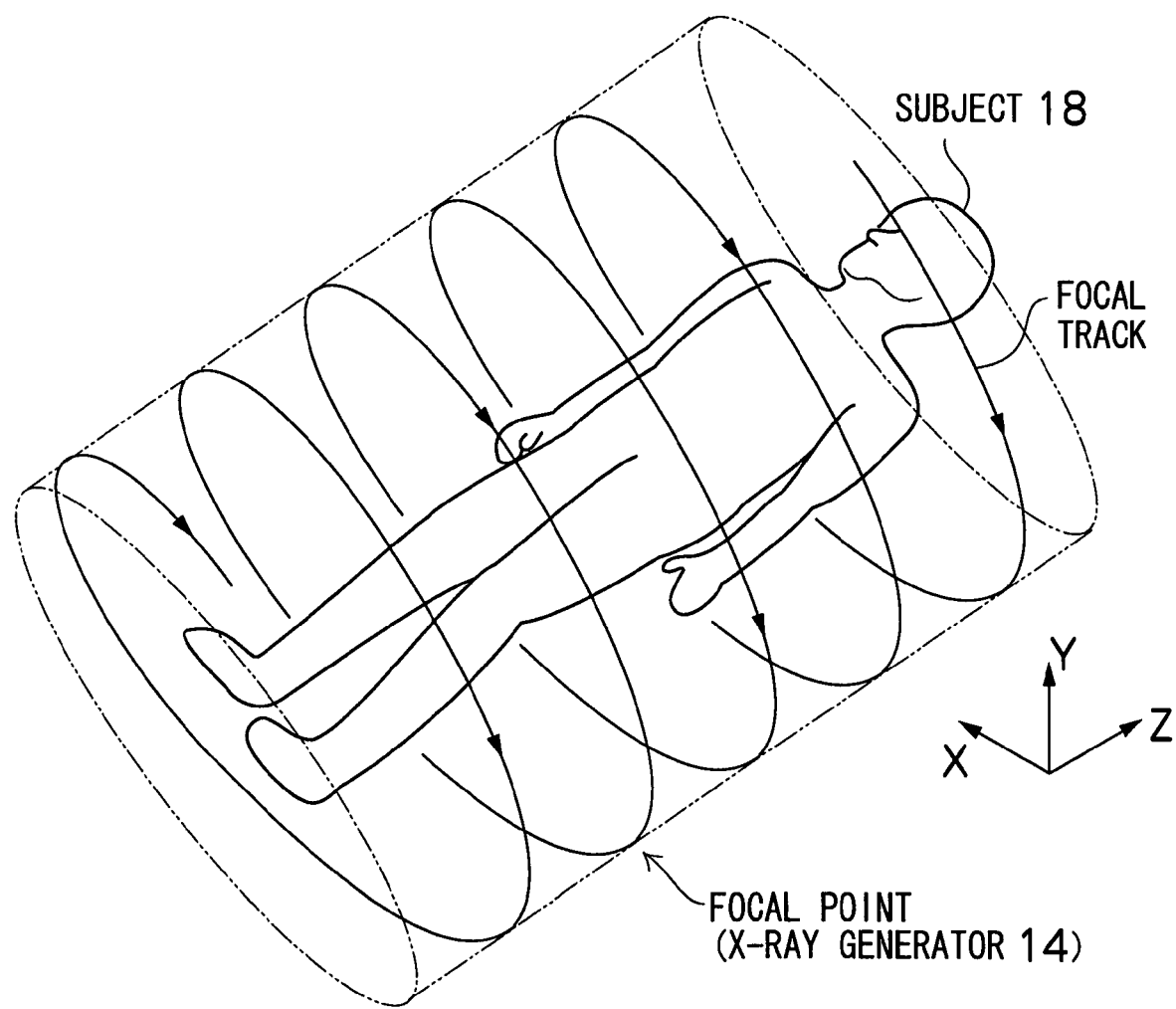
FIG. 3 illustrates a helical scanning by the multi-array detector X-ray CT apparatus.
Figure 4A:
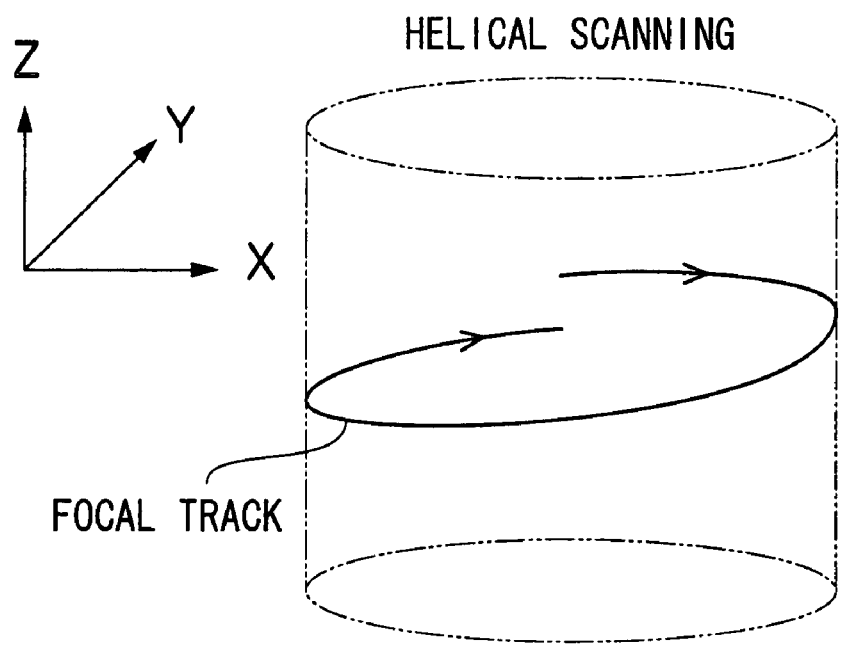
FIG. 4(*a*) and FIG. 4(*b*) respectively illustrate a normal scanning and a helical scanning by the multi-array detector CT apparatus.
Figure 4B:
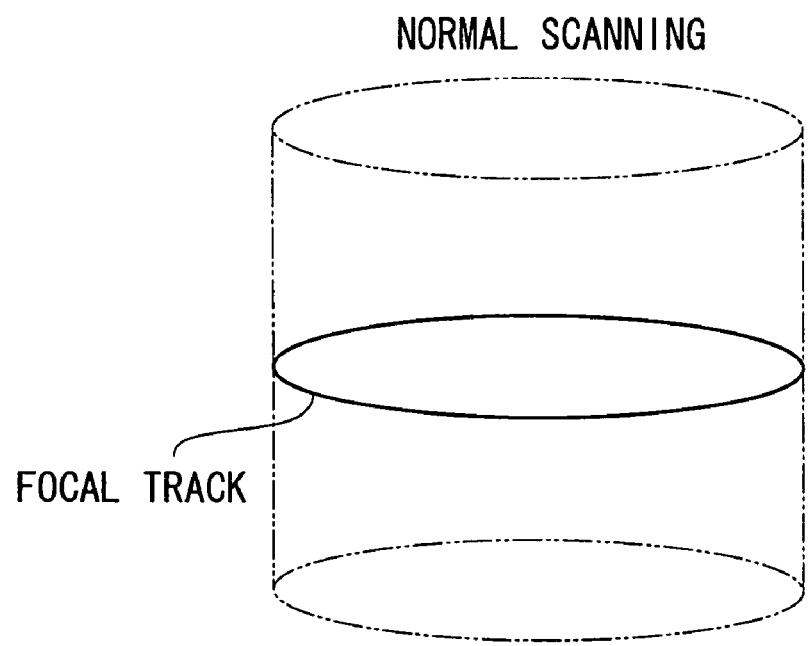

With reference to FIG. 3, FIG. 4(a) and FIG. 4(b), a helical scanning carried out by the X-ray CT apparatus 10 will be explained. In the following explanations, the origin of the coordinate system is fixed to the subject 18. The helical scanning collects projection data while clockwise rotating the scanner 12 in FIG. 1 and moving the subject table 26 in the Z-direction in FIG. 2. At this time, the X-ray generator 14, i.e., focal point of generated X-rays, describes a helical track as shown in FIG. 3 and FIG. 4(a) relative to the subject 18. The ratio of the distance T that the subject table 26 moves while the scanner 12 once rotates the detector collimation thickness D (see FIG. 2) is called a "helical pitch p":

$p = T/D.$

During a normal scanning rotating only the scanner 12 without moving the subject table 26, the focal point of X-rays depicts a circular track shown in FIG. 4(b). When an image is reconstructed using projection data collected by a helical scanning, artifacts appear in a tomogram obtained due to influences of helical distortion. To prevent this artifact, the projection data is corrected through an interpolation calculation which corrects the helical track of an X-ray focus to a circular track and the corrected projection data is used to reconstruct an image. This correction is generally called "helical correction."

Figure 5A:
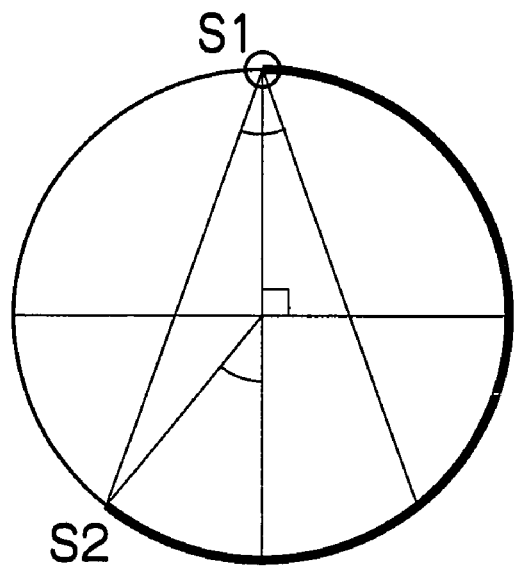
FIG. 5(*a*) and FIG. 5(*b*) respectively illustrate 180-degree reconstruction using a fan beam and 180-degree reconstruction using a parallel beam by the multi-array detector CT apparatus.
Figure 5B:
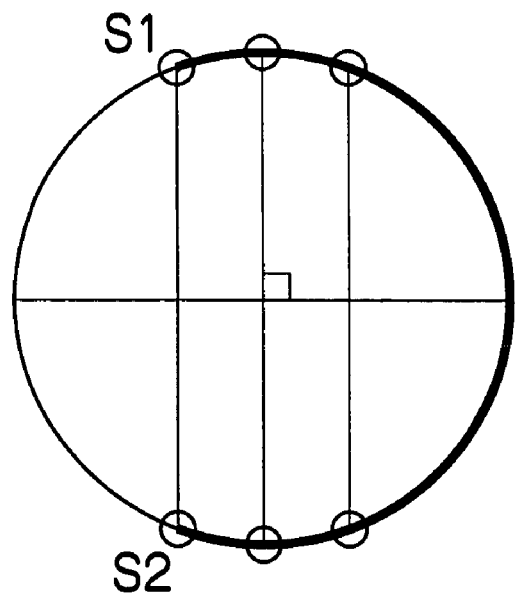

In a third-generation CT, an X-ray irradiated from an X-ray generator is a fan beam as shown in FIG. 5(a). For example, a parallel beam obtained by rearranging the fan beam with a process called "rebining" to speed up the calculation as shown in FIG. 5(b) may be used. In either case of the fan beam or parallel beam, the minimum projection angle necessary to reconstruct an image is an angle from S1 to S2 (180-degree ($\pi$)+fan angle). On the other hand, reconstructing an image from projection data collected at this minimum projection angle is generally called "180-degree reconstruction" or "half-scan reconstruction" and the respective images obtained are generally called a "180-degree reconstructed image" or "half-scan image." Reconstructing an image from projection data corresponding to 360-degree ($2\pi$) is generally called "360-degree reconstruction" or "full-scan reconstruction" and the respective images obtained are generally called a "360-degree reconstructed image" or "full-scan image." The 180-degree reconstruction can also be realized by normalizing redundant data from projection data corresponding to angles greater than the minimum projection angle and smaller than 360-degree.

With reference to FIG. 6(a) and FIG. 6(b), a method for collecting projection data through a helical scanning using the multi-array detector X-ray CT apparatus 10 will be explained. When a helical scanning is carried out by the multi-array detector X-ray CT apparatus 10, a plurality of detector element arrays R1 to R8 pass through the same slice position at different phases. Therefore, projection data corresponding to 360-degree and projection data corresponding to 180-degree are divided by phases in 360-degree reconstruction and 180-degree reconstruction, respectively and an image is reconstructed using the projection data collected from a plurality of detector element arrays about the respective phases.

FIG. 6(a) shows a case where 360-degree reconstruction is performed using the projection data collected from all the detector element arrays R1 to R8 and FIG. 6(b) shows a case where 180-degree reconstruction is performed using the projection data collected from the detector element arrays R4 to R7. In this example, the helical pitch is 8. Since the helical pitch is the ratio of the distance the subject moves while the X-ray source and detector array make one rotation to the distance between the detector arrays, when the helical pitch is 8, projection data corresponding to one revolution ($2\pi$) can be acquired when there are eight detector arrays. To acquire projection data corresponding to 180-degree phase which is a minimum data range necessary for reconstruction, it is necessary to set the helical pitch to twice or less than the number of detector arrays.

In FIG. 6(a) and FIG. 6(b), thin solid lines represent measuring lines of the respective detector element arrays and bold solid lines represent a range of data used to reconstruct an image. As is clear from FIG. 6(b), when 180-degree reconstruction is done in a helical scanning with helical pitch 8, an image can be reconstructed using only four arrays of data (the phase angle range of 5π/8 to 13π/8 in the example in FIG. 6(b)). This is equivalent to generating data corresponding to 360-degree by complementing data at an opposite position with the data corresponding to 180-degree and carrying out 360-degree reconstruction based thereupon.

By selecting the range of arrays using data from among the detector element arrays R1 to R8 (e.g., R2 to R5, R3 to R6, etc.), it is possible to change the phase range of data (from projection start phase to projection end phase). Data in different phase ranges thus created by changing the range of arrays in which data is used is called "data of different phases." It is possible to reconstruct an image in the range of different phase angles from these data of different phases.

Figure 7A:
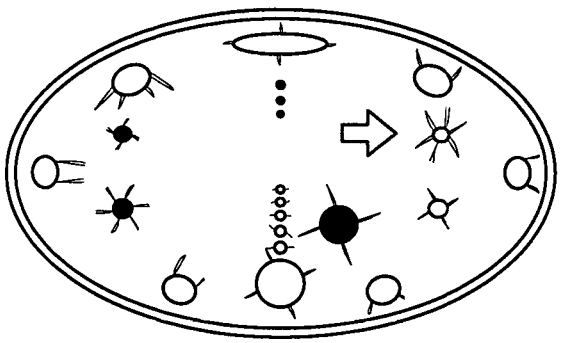
FIG. 7(*a*) to FIG. 7(*e*) illustrate images by 180-degree reconstruction whose projections are started from different angles in a helical scanning.
Figure 7B:
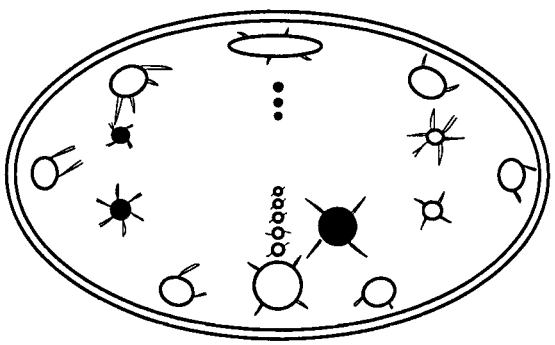
Figure 7C:
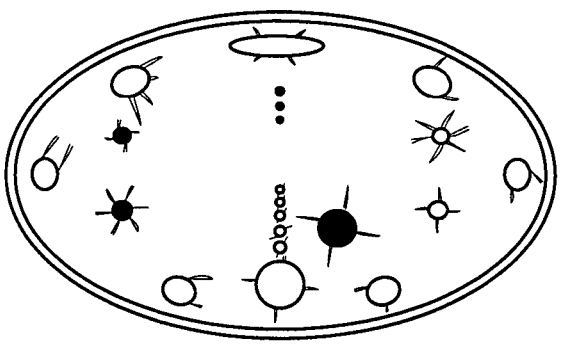
Figure 7D:
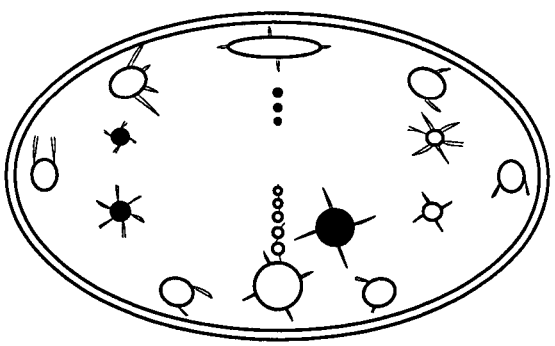
Figure 7E:
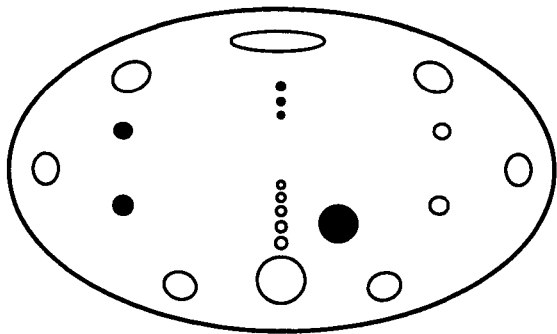

FIGS. 7(a) to 7(d) schematically show examples of 180-degree reconstructed images obtained by carrying out a helical scanning on a phantom having the cross section shown in FIG. 7(e) and starting projections from different angles. FIGS. 7(a), 7(b), 7(c) and 7(d) are a 0π phase image reconstructed from data of a phase angle range from 0π to π, a π/6 phase image reconstructed from data of an angle range from π/6 to 7π/6, a π/3 phase image reconstructed from data of a phase angle range from π/3 to 4π/3 and a π/2 phase image reconstructed from data of a phase angle range from π/2 to 3π/2. When attention is focused on an artifact produced at the position indicated by an arrow in FIG. 7(a), it is understandable that the direction in which the artifact is produced changes as the phase angle advances from FIGS. 7(b) to 7(c) and FIG. 7(d).

Figure 8A:
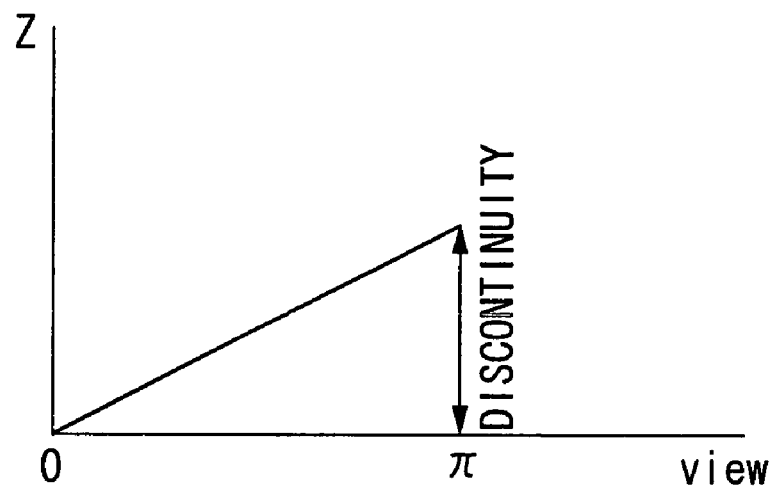
FIG. 8(*a*) and FIG. 8(*b*) illustrate a measurement chart and a data weighting function of a helical scanning which carries out 180-degree reconstruction in a conventional technique.
Figure 8B:
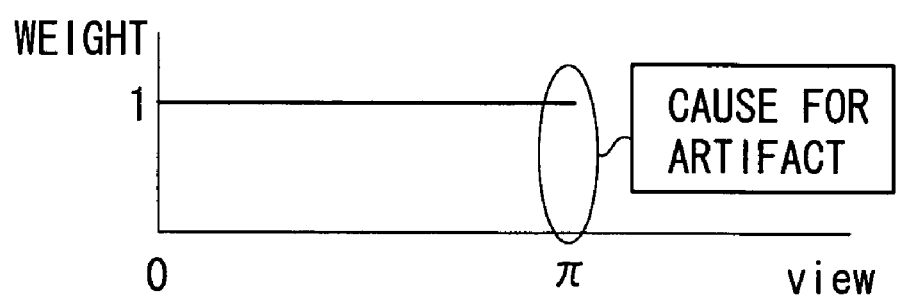

The cause for this artifact will be explained with reference to FIGS. 8(a) and 8(b). FIG. 8(a) illustrates a measurement chart of a helical scanning carrying out 180-degree reconstruction in a phase angle range from 0π to π and the vertical axis represents the Z-position and the horizontal axis represents the phase respectively. FIG. 8(b) illustrates a data weighting function of conventional 180-degree reconstruction and the vertical axis represents the weight and the horizontal axis represents the phase. In a helical scanning shown in FIG. 8(a), the position of the X-ray source is shifted in the Z-direction between the projection start phase and projection end phase, and therefore the data in the phase direction is discontinuous at both ends. In the projection example shown in FIG. 6(b), the data of R4 at the opposite position is used as the phase data following R4, R5, R6 and R7. There is a phase difference of 180-degree between R7 and R4 and also a difference in the track of the X-ray beam which becomes the origin of data, and therefore the data becomes discontinuous between R7 and R4. In the 180-degree reconstruction shown in FIG. 8(a), when data normalization in the phase direction is considered, there is only data corresponding to 180-degree, and therefore data weighting is always 1 for each phase as shown in FIG. 8(b). In this case, a streak artifact appears at discontinuous phases. When the phase angle range of data used to reconstruct an image (from projection start phase to projection end phase) changes, the discontinuous phase changes and the phase of the artifact generated changes accordingly.

In the method of reconstructing an image according to the embodiment of the present invention, to reduce the discontinuity of the data and suppress artifacts explained in FIGS. 8(a) and 8(b), the data of different phases in a phase range wider than π is calculated and combined. As explained in FIGS. 7(a) to 7(d), the phases at which artifacts are generated vary from one piece of data of different phases to another, and therefore by combining data pieces of different phases, the intensity of artifacts is reduced.

In the embodiment of the present invention, the data in the phase angle range from 0π to π (hereinafter referred to as "phase range I") shown in FIG. 9(a) and the data in the phase angle range from π/2 to 3π/2 (hereinafter referred to as "phase range II") are weighted using the weighting function shown in FIG. 9(b) and used to reconstruct an image, wherein images may be reconstructed starting from data not weighted, and the reconstructed images may be weighted and combined. According to this weighting function, the weight of the data in the phase range I is 0 at both ends in the phase direction, i.e., 0π and π and the weight is 1 at the center in the phase direction, i.e., π/2. Furthermore, the weight of the data in the phase range II is 0 at both ends in the phase direction, i.e., π/2 and 3π/2 and the weight is 1 at the center in the phase direction, i.e., π. That is, the weight of data at the end of each data piece in the phase direction having discontinuity causing artifacts is reduced to reduce contribution to image reconstruction. Thus, using data in a plurality of phase angle ranges by adding them in the phase direction and effectively reducing the weight at the end of data can reduce artifacts caused by discontinuity at the end of data.

Figure 9A:
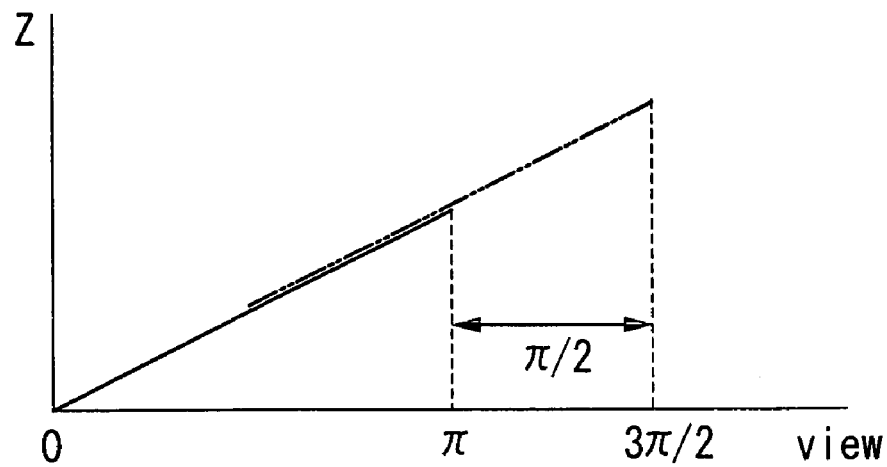
FIG. 9(*a*) and FIG. 9(*b*) illustrate a measurement chart and a data weighting function of a helical scanning which carries out reconstruction using a phase addition method according to an embodiment of the present invention.
Figure 9B:
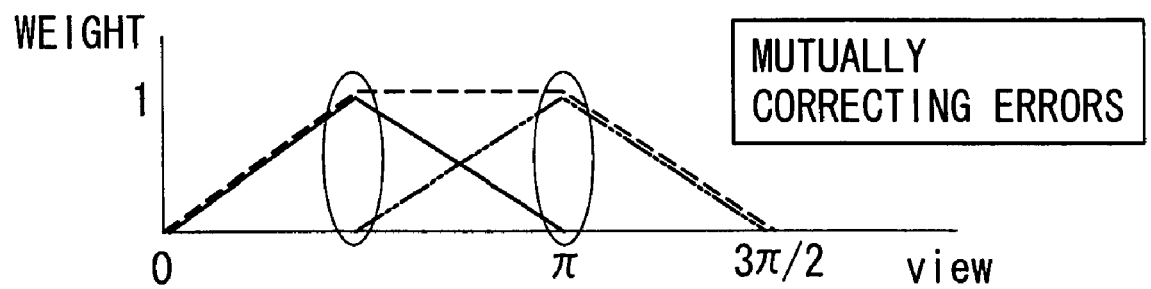

In the example shown in FIG. 9(a), the end of the phase range II (that is, the position corresponding to the least continuity of data in the phase range II) matches the center of the phase range I, namely, the position corresponding to the highest continuity of data in the phase range I, and therefore the correction effect is highest. Thus, when the whole data generated by adding data pieces of different phases corresponds to a 3π/2 phase, the correction effect becomes highest.

Figure 10A:
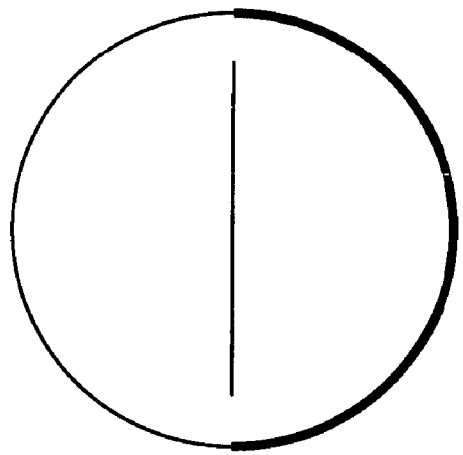
FIG. 10(a) to FIG. 10(d) conceptually illustrate an addition of data in a plurality of phase angle ranges.
Figure 10B:
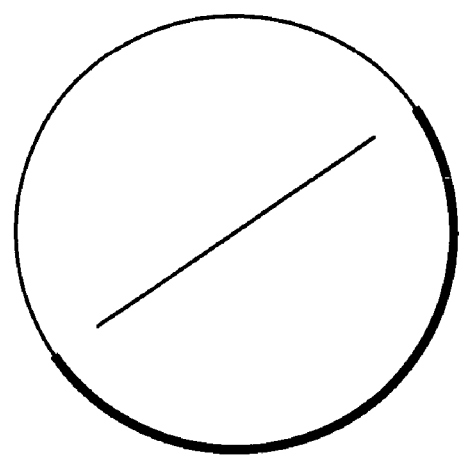
Figure 10C:
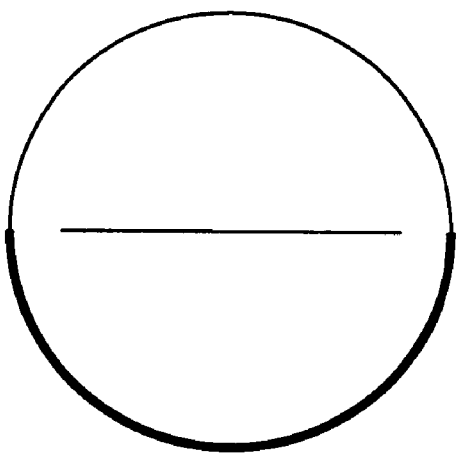
Figure 10D:
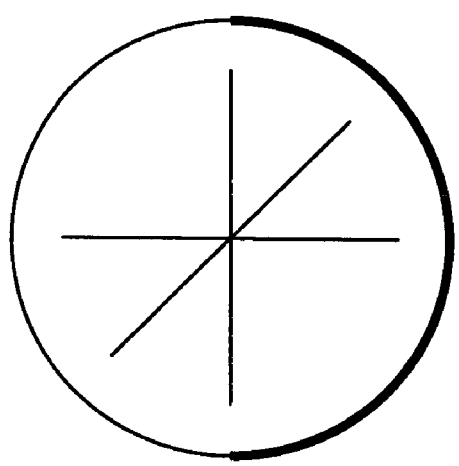

With reference to FIGS. 10(a) to 10(d), additions of data in a plurality of phase angle ranges will be explained conceptually. FIGS. 10(a), 10(b) and 10(c) conceptually illustrate a π/2 phase image, 3π/4 phase image and π phase image, respectively. An artifact at an angle corresponding to the phase is generated in each image. FIG. 10(d) is an image obtained by averaging these three images of different phases and such averaging processing reduces the intensity of the artifact to ⅓.

Figure 11:
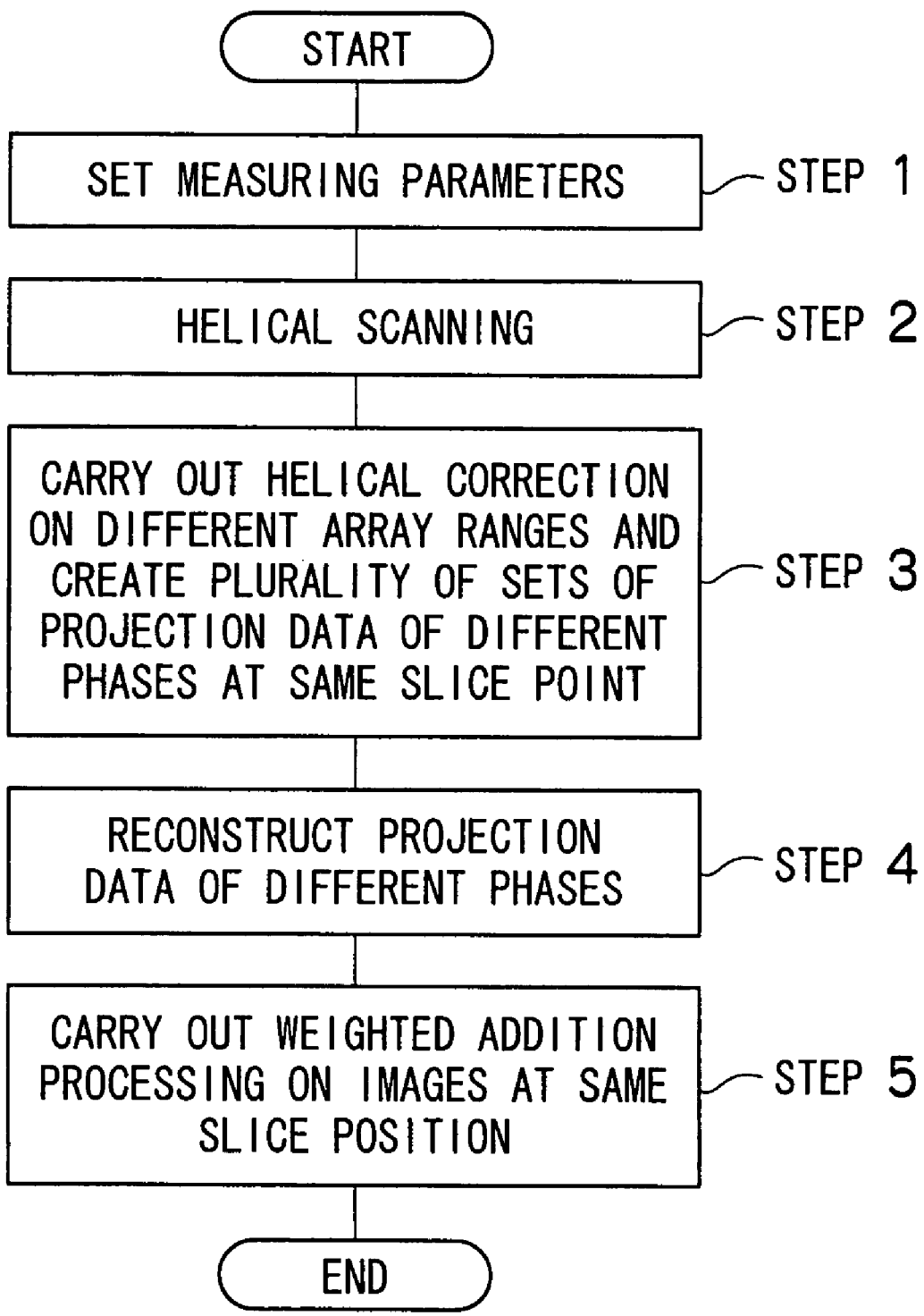
FIG. 11 is a flow chart illustrating a reconstructed image addition method.

A specific procedure for image reconstruction according to the embodiment of the present invention will be explained with reference to FIG. 11 to FIG. 13. FIG. 11 is a flow chart when image reconstruction is performed starting from data not weighted and reconstructed images obtained are weighted and combined. First, measuring parameters are set by the input apparatus 40 (STEP 1). Examples of measuring parameters include helical pitch p (or moving velocity of the subject table 26), detector collimator thickness D, image-taking range (effective range of field of view), tube current and tube voltage of the X-ray generator 14 and scanning time (time required for the scanner 12 to make one rotation). Then, a helical scanning is carried out based on the set measuring parameters (STEP 2), a plurality of sets of projection data of different phases at the same slice position are created from the projection data of each array obtained (STEP 3), the projection data of different phases obtained are reconstructed and a plurality of reconstructed images at the same slice position are obtained (STEP 4). Then, the plurality of reconstructed images obtained are subjected to weighted addition processing and final reconstructed images are obtained (STEP 5).

Figure 12:
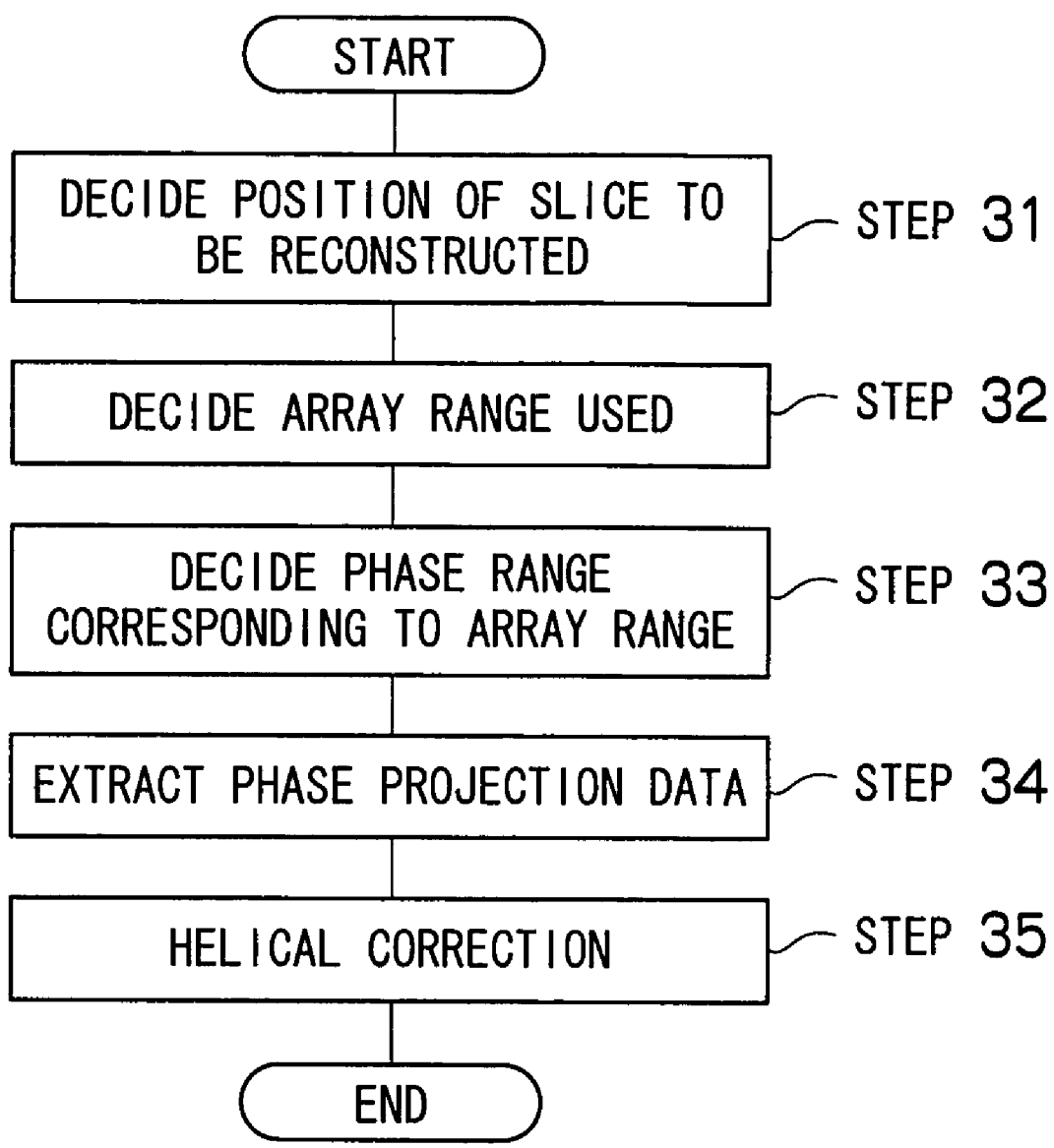
FIG. 12 is a flow chart illustrating a projection data addition method.

FIG. 12 is a flow chart illustrating details of the processing carried out in STEP 3 in FIG. 11. After a helical scanning is carried out in STEP 2 in FIG. 11, positions of slices to be reconstructed are decided to obtain data of different phases at a certain slice position (STEP 31). The position of this reconstructed slice is determined by the image-taking range input from the input apparatus 40 and the distance between the reconstructed slices and defined by the distance from an image-taking start reference position in the Z-direction. For example, when images are generated from an image-taking start reference position at intervals of 1 mm from the position of the image-taking range lower limit $L_{min}$=50 mm to the position of the image-taking range upper limit $L_{max}$=100 mm, the reconstructed slice position $R_{pos}$ is as follows:

$$R_{pos}=L_{min}+i(i=0, 1, 2, 3, \ldots, (L_{max}-L_{min}))$$

Then, the array range of the data used for reconstruction of the determined slices is determined (STEP 32). At this time, the range of the detector array used for reconstruction is determined such that the number of detector arrays equal to or greater than half the helical pitch are included, wherein the upper limit of the number is the number of detector arrays of the X-ray CT apparatus 10. For example, in order for an eight-array detector to obtain 180-degree data at a certain phase when the helical pitch is 8, data corresponding to four arrays which is half the helical pitch becomes 180-degree phase data, and therefore R1 to R4, R2 to R5, R3 to R6, R4 to R7 and R5 to R8, etc., are determined as the array ranges.

Then, a phase range is determined using the phase at which the position of the slice to be reconstructed in the data in the determined array range matches the position of the rotation center of each detector data as a reference (STEP 33) and the data of the corresponding array range and phase range is acquired as the phase data (STEP 34). The data in a plurality of phase ranges obtained here are data of different phases having the same slice position and different phase ranges.

The data of different phases obtained is detector data corresponding to four arrays, and therefore by creating a weighting function for a four-array detector (4-array multi, helical pitch 8) disclosed in International Publication WO01/28425 and respectively assigning the weighting functions to four-array data (phase data), helically-corrected projection data (array of weighted projection data) is obtained (STEP 35).

FIG. 13 is a flow chart for weighting projection data of different phases and reconstructing an image from the data. STEP 1 to STEP 3 are the same as those in FIG. 11. In FIG. 13, a plurality of sets of projection data of different phases obtained in STEP 3 are subjected to weighted addition processing (STEP 6) and the projection data obtained is reconstructed to obtain a final reconstructed image (STEP 7).

In the above, the plurality of phase ranges of projection data may also include overlapping portions. Furthermore, data of different phases are all made up of 180-degree phase data, but it is also possible to use different phase ranges of 180-degree or greater (e.g., 180-degree phase data, 200-degree phase data, 250-degree phase data) for all data. Data of different phases only need to have at least a minimum data range (180-degree phase) necessary for reconstruction.

In this embodiment, an array of weighted projection data is obtained by obtaining 8 arrays of projection data from detectors made up of eight detector element arrays and applying a weighted function to the projection data. However, this embodiment is not limited to this and it is also possible to obtain an array of weighted projection data by obtaining two or more arrays of projection data from a multi-array detector made up of two or more detector element arrays or a planar detector and applying a weighting function to these arrays. The helical pitch of a helical scanning is not limited to an integer value, but may also be a decimal value (e.g., 1.5, 2.5, etc.).

INDUSTRIAL APPLICABILITY

As described above, according to the multi-array detector X-ray CT apparatus and the method for creating the tomogram according to the present invention, it is possible to suppress artifacts and obtain a good image by combining data of different phases or images reconstructed from the data.

The invention claimed is:

1. An X-ray CT apparatus comprising:
a scanner that includes an X-ray source and an X-ray detector having two-dimensionally arranged X-ray detector elements, disposed on an opposite side of the X-ray source interposing a subject to be examined therebetween, and provided for measuring X-rays irradiated front the X-ray source onto the subject and passed through the subject and carries out helical scanning by rotating the X-ray source and the X-ray detector relative to the subject around a revolving axis and moving the subject relative to the X-ray source and the X-ray detector along the revolving axis; and
an image processor for creating a tomogram of the subject from projection data collected by helical scanning using the X-ray detector,
wherein the image processor creates a tomogram by reconstructing data combining a plurality of different sets of projection data in a plurality of different phase ranges of a revolution at a point on the subject on the revolving axis.

2. The X-ray CT apparatus according to claim 1, wherein the image processor reconstructs an image from data weighted and combined using the plurality of different sets of projection data and weighting functions which are functions of corresponding phase ranges of the revolution.

3. The X-ray CT apparatus according to claim 2, wherein the phase ranges of the revolution of the plurality of different sets of projection data extend over a range of $3\pi/2$ or more of a complete phase.

4. The X-ray CT apparatus according to claim 1, wherein the image processor includes a selection device which selects the plurality of different sets of projection data from a plurality of the two-dimensionally arranged X-ray detector element arrays and an image is reconstructed using detected data of the element arrays selected by the selection device and data opposite to the detected data.

5. An X-ray CT apparatus comprising:
a scanner that includes an X-ray source and an X-ray detector having two-dimensionally arranged X-ray detector elements, disposed on an opposite side of the X-ray source interposing a subject to be examined therebetween, and provided for measuring X-rays irradiated from the X-ray source onto the subject and passed through the subject and carries out helical scanning by rotating the X-ray source and the X-ray detector relative to the subject around a revolving axis and moving the subject relative to the X-ray source and the X-ray detector along the revolving axis; and
an image processor for creating a tomogram of the subject from projection data collected by helical scanning using the X-ray detector, wherein the image processor creates a tomogram by reconstructing images in a plurality of different phase ranges of a revolution at a point on the subject on the revolving axis from a plurality of different sets of projection data in the plurality of different phase ranges and combining the reconstructed images in the plurality of different phase ranges.

6. The X-ray CT apparatus according to claim 5, wherein the images in the plurality of different phase ranges are weighted by weighting functions which are functions of the phase ranges of the revolution and combined to obtain the tomogram.

7. The X-ray CT apparatus according to claim 5, wherein the image processor includes a selection device that selects the plurality of different sets of projection data from a plurality of the two-dimensionally arranged X-ray detector element arrays and reconstructs the images using the detected data of the element arrays selected by the selection device and data opposite to the detected data.

8. The X-ray CT apparatus according to claim 5, wherein the different phase range for the reconstructed images in the plurality of different phase ranges is 180-degree.

9. A method for creating a tomogram of a subject by revolving an X-ray source relative to the subject around a revolving axis and carrying out helical scanning which moves the X-ray source relative to the subject along the revolving axis from projection data collected by an X-ray detector made up of a plurality of two-dimensionally arranged detector elements for measuring X-rays which have been irradiated from the X-ray source onto the subject and have passed through the subject, comprising:
 a step of setting measuring parameters of the projection data;
 a step of obtaining the projection data by carrying out helical scanning based on the measuring parameters;
 a step of creating a plurality of different sets of projection data in a plurality of different phase ranges of a revolution at a point on the subject on the revolving axis from the projection data;
 a step of creating a plurality of reconstructed images at the point corresponding to the plurality of different sets of projection data created; and
 a step of creating a reconstructed/added image by applying a weighting function to and adding the plurality of reconstructed images created.

10. The method for creating a tomogram according to claim 9, wherein the step of creating the plurality of different sets of projection data comprises:

a step of setting the point of the reconstructed subject on the revolving axis;
 a step of deciding a range of a plurality of arrays of the two-dimensionally arranged X-ray detector elements of the data used for reconstruction of the set point;
 a step of deciding a phase range corresponding to the decided range of the arrays of the X-ray detector elements;
 a step of acquiring the data of the range of the arrays and the phase range as phase data; and
 a step of acquiring helically corrected projection data by creating and applying the weighting function which is a function of phases on the revolving axis to the phase data.

11. The method for creating a tomogram according to claim 10, wherein the weighting function is a phase addition weighting function.

12. The method for creating a tomogram according to claim 11, wherein the phase range of the weighting function is $\pi$ or more.

13. A method for creating a tomogram of a subject by revolving an X-ray source relative to the subject around a revolving axis and carrying out helical scanning which moves the X-ray source relative to the subject along the revolving axis from projection data collected by an X-ray detector made up of a plurality of two-dimensionally arranged detector elements for measuring X-rays which have been irradiated from the X-ray source onto the subject and have passed through the subject, comprising:
 a step of setting measuring parameters of the projection data;
 a step of obtaining the projection data by carrying out helical scanning based on the measuring parameters;
 a step of creating a plurality of different sets of projection data in a plurality of different phase ranges of a revolution at a point on the subject on the revolving axis from the projection data;
 a step of applying a weighting function to and adding the plurality of different sets of projection data created; and
 a step of creating a reconstructed image using the data obtained by applying the weighting function and adding.

* * * * *